(12) United States Patent
Anderson et al.

(10) Patent No.: US 9,764,118 B2
(45) Date of Patent: Sep. 19, 2017

(54) GUIDE EXTENSION CATHETER

(71) Applicant: BOSTON SCIENTIFIC SCIMED, INC., Maple Grove, MN (US)

(72) Inventors: James M. Anderson, Corcoran, MN (US); Huisun Wang, Maple Grove, MN (US); Derek C. Sutermeister, Ham Lake, MN (US); Steven J. Koch, Zimmerman, MN (US); Benjamin P. Gundale, Plymouth, MN (US); Paul J. Miller, Vadnais Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 129 days.

(21) Appl. No.: 14/667,120

(22) Filed: Mar. 24, 2015

(65) Prior Publication Data
US 2015/0190617 A1 Jul. 9, 2015

Related U.S. Application Data

(63) Continuation of application No. 13/755,989, filed on Jan. 31, 2013, now Pat. No. 8,996,095.
(Continued)

(51) Int. Cl.
*A61M 25/01* (2006.01)
*A61M 25/06* (2006.01)
(Continued)

(52) U.S. Cl.
CPC .... *A61M 25/0662* (2013.01); *A61M 25/0009* (2013.01); *A61M 25/0052* (2013.01);
(Continued)

(58) Field of Classification Search
CPC .......... A61M 25/09; A61M 2025/0681; A61M 2025/09175; A61M 2025/09083; A61M 25/0052
(Continued)

(56) References Cited

U.S. PATENT DOCUMENTS 4,564,014 A 1/1986 Fogarty et al.
4,616,652 A 10/1986 Simpson
(Continued)

FOREIGN PATENT DOCUMENTS

DE 3819372 C1 1/1990
EP 0277366 A1 8/1988
(Continued)

*Primary Examiner* — Gerald Landry, II
(74) *Attorney, Agent, or Firm* — Seager, Tufte & Wickhem LLP

(57) ABSTRACT

Medical devices and methods for making and using medical devices are disclosed. An example medical device may include a guide extension catheter. The guide extension catheter may include a push member having a proximal portion with a proximal stiffness, a distal portion with a distal stiffness different from the proximal stiffness, and a transition portion disposed between the proximal portion and the distal portion. The transition portion may provide a smooth transition between the proximal stiffness and the distal stiffness. The push member may have a first outer diameter. A distal tubular member may be attached to the push member. The distal tubular member may have a second outer diameter larger than the first outer diameter.

18 Claims, 22 Drawing Sheets

Related U.S. Application Data

(60) Provisional application No. 61/593,124, filed on Jan. 31, 2012.

(51) Int. Cl.
  *A61M 25/00* (2006.01)
  *A61M 25/04* (2006.01)
  *A61B 17/12* (2006.01)
  *A61B 17/00* (2006.01)

(52) U.S. Cl.
  CPC ........ *A61M 25/0069* (2013.01); *A61M 25/01* (2013.01); *A61M 25/0105* (2013.01); *A61M 25/04* (2013.01); *A61B 17/1204* (2013.01); *A61B 17/12136* (2013.01); *A61B 2017/00526* (2013.01); *A61M 2025/0681* (2013.01); *F04C 2270/0421* (2013.01)

(58) Field of Classification Search
  USPC ........ 600/434, 585; 604/264, 510, 523, 526, 604/528
  See application file for complete search history.

(56) References Cited

U.S. PATENT DOCUMENTS

| | | | |
|---|---|---|---|
| 4,762,129 A | 8/1988 | Bonzel | |
| 5,120,323 A | 6/1992 | Shockey et al. | |
| 5,232,445 A | 8/1993 | Bonzel | |
| 5,238,004 A | 8/1993 | Sahatjian et al. | |
| 5,267,982 A | 12/1993 | Sylvanowicz | |
| 5,338,300 A * | 8/1994 | Cox | A61M 25/104 604/103.05 |
| 5,385,562 A | 1/1995 | Adams et al. | |
| 5,441,489 A | 8/1995 | Utsumi et al. | |
| 5,458,584 A * | 10/1995 | Ginn | A61B 8/06 604/528 |
| 5,527,292 A | 6/1996 | Adams et al. | |
| 5,613,948 A * | 3/1997 | Avellanet | A61M 25/1002 604/103.07 |
| 5,772,609 A | 6/1998 | Nguyen et al. | |
| 6,066,126 A | 5/2000 | Li et al. | |
| 6,139,510 A | 10/2000 | Palermo | |
| 6,290,693 B1 * | 9/2001 | Jung, Jr. | A61N 5/1002 600/585 |
| 6,508,803 B1 | 1/2003 | Horikawa et al. | |
| 6,575,958 B1 | 6/2003 | Happ et al. | |
| 6,638,268 B2 | 10/2003 | Niazi | |
| 6,695,793 B2 | 2/2004 | Brennan et al. | |
| 6,953,454 B2 | 10/2005 | Peterson et al. | |
| 7,294,124 B2 | 11/2007 | Eidenschink | |
| 7,316,678 B2 | 1/2008 | Nash et al. | |
| 7,717,899 B2 | 5/2010 | Bowe et al. | |
| 7,762,984 B2 | 7/2010 | Kumoyama et al. | |
| 8,048,032 B2 | 11/2011 | Root et al. | |
| 8,142,412 B2 | 3/2012 | Hehrlein et al. | |
| 8,142,413 B2 | 3/2012 | Root et al. | |
| 8,292,850 B2 | 10/2012 | Root et al. | |
| 2004/0116832 A1 | 6/2004 | Friedrich et al. | |
| 2004/0236215 A1 * | 11/2004 | Mihara | A61M 25/0068 600/434 |
| 2005/0065437 A1 | 3/2005 | Weber et al. | |
| 2005/0070844 A1 | 3/2005 | Chow et al. | |
| 2005/0267442 A1 | 12/2005 | Von Oepen | |
| 2006/0173475 A1 | 8/2006 | Lafontaine et al. | |
| 2006/0259117 A1 * | 11/2006 | Pal | A61F 2/95 623/1.11 |
| 2007/0093781 A1 * | 4/2007 | Kugler | A61B 17/221 604/510 |
| 2007/0114211 A1 * | 5/2007 | Reynolds | A61M 25/09 219/121.13 |
| 2007/0260219 A1 * | 11/2007 | Root | A61M 25/0026 604/523 |
| 2007/0299367 A1 * | 12/2007 | Melsheimer | A61L 31/022 600/585 |
| 2008/0167628 A1 * | 7/2008 | Li | A61F 2/95 604/264 |
| 2009/0177120 A1 | 7/2009 | Tockman et al. | |
| 2009/0264865 A1 * | 10/2009 | Kawai | A61M 25/0105 604/528 |
| 2010/0217237 A1 * | 8/2010 | Itou | A61B 17/22 604/540 |
| 2010/0324539 A1 * | 12/2010 | Lupton | A61M 25/09 604/528 |
| 2011/0004207 A1 | 1/2011 | Wallace et al. | |
| 2011/0172520 A1 | 7/2011 | Lentz | |
| 2011/0265943 A1 | 11/2011 | Rosqueta et al. | |
| 2011/0301502 A1 * | 12/2011 | Gill | A61F 2/95 600/585 |
| 2011/0319926 A1 | 12/2011 | Becking et al. | |
| 2012/0029628 A1 | 2/2012 | Rowe | |
| 2012/0046575 A1 | 2/2012 | Brown | |
| 2012/0150271 A1 * | 6/2012 | Fischell | A61M 25/09 623/1.11 |
| 2012/0316585 A1 * | 12/2012 | Jeffrey | A61M 25/005 606/159 |

FOREIGN PATENT DOCUMENTS

| | | |
|---|---|---|
| JP | 2005524418 A | 8/2005 |
| JP | 2008142351 A | 6/2008 |
| JP | 2008536640 A | 9/2008 |
| JP | 2011135989 A | 7/2011 |
| JP | 2012501690 A | 1/2012 |
| WO | 03037415 A1 | 5/2003 |
| WO | 03049798 A2 | 6/2003 |
| WO | 2006113868 A2 | 10/2006 |
| WO | 2010028090 A2 | 3/2010 |

* cited by examiner

GUIDE EXTENSION CATHETER

CROSS-REFERENCE TO RELATED APPLICATIONS

This application is a continuation of U.S. patent application Ser. No. 13/755,989, filed on Jan. 31, 2013, now U.S. Pat. No. 8,996,095, which claims priority from the earlier filed U.S. Provisional Application No. 61/593,124, filed Jan. 31, 2012 which hereby incorporated into this application by reference as if fully set forth herein.

TECHNICAL FIELD

The present disclosure pertains to medical devices, and methods for manufacturing medical devices. More particularly, the present disclosure pertains to elongated intracorporeal medical devices including a guide extension catheter.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include a guide extension catheter. The guide extension catheter may include a push member having a proximal portion with a proximal stiffness, a distal portion with a distal stiffness different from the proximal stiffness, and a transition portion disposed between the proximal portion and the distal portion. The transition portion may provide a smooth transition between the proximal stiffness and the distal stiffness. The push member may have a first outer diameter. A distal tubular member may be attached to the push member. The distal tubular member may have a second outer diameter larger than the first outer diameter.

An example guide extension catheter system is also disclosed. The guide extension catheter system may include a proximal shaft having a rail member formed thereon. The proximal shaft may have an outer diameter. A removable push member may be releasably attached to the proximal shaft and coupled to the rail portion. A distal sheath may be coupled to the proximal shaft. The distal sheath may have an outer diameter greater than the outer diameter of the proximal shaft.

Methods for accessing a coronary artery are also disclosed. An example method may include providing a guide catheter and advancing the guide catheter through a blood vessel to a position adjacent to an ostium of a coronary artery. The method may also include providing a guide extension catheter. The guide extension catheter may include a proximal shaft having a rail member formed thereon, a removable push member releasably attached to the proximal shaft and coupled to the rail portion, and a distal sheath coupled to the proximal shaft. The proximal shaft may have an outer diameter. The distal sheath may have an outer diameter greater than the outer diameter of the proximal shaft. The method may also include advancing the guide extension catheter through the guide catheter to a position where at least a portion of the distal sheath extends distally beyond a distal end of the guide catheter and into the coronary artery and advancing a treatment catheter through the guide catheter.

Methods for manufacturing a guide extension catheter are also disclosed. An example method may include providing a proximal shaft having a proximal outer diameter and providing a distal shaft having a distal outer diameter. The distal outer diameter may be greater than the proximal outer diameter. The method may also include disposing a polymeric tube over a portion of the proximal shaft and a portion of the distal shaft and reflowing the polymeric tube to form a joint that attaches the proximal shaft and the distal shaft. The joint may be free of a weld.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
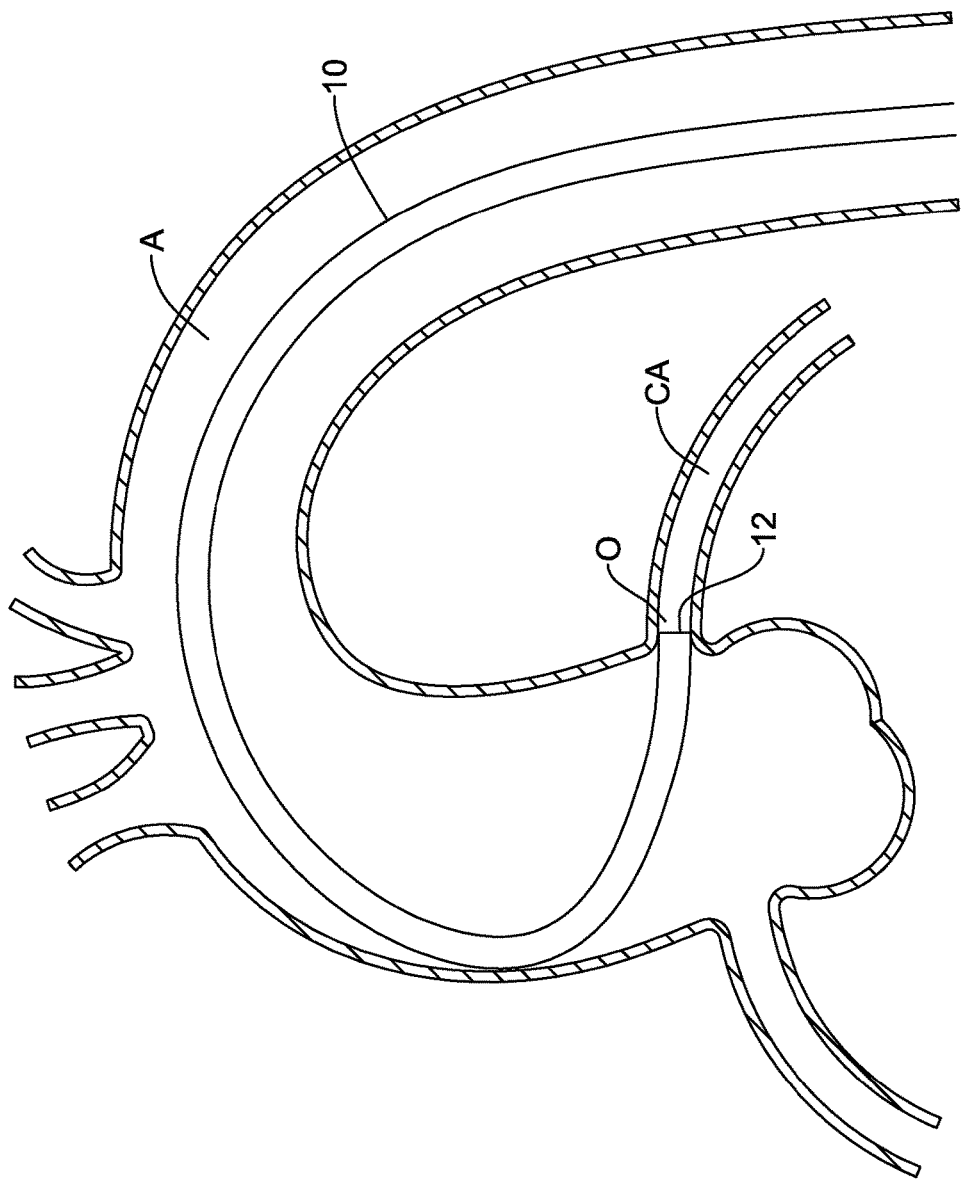
FIG. 1 is a plan view illustrating an example guide catheter advanced through the aorta to the ostium of a coronary artery.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5). As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Minimally-invasive cardiac interventions such as percutaneous transluminal coronary angioplasty are widely utilized throughout the world. These procedures may include the use of a guide catheter. For example, a guide catheter 10 may be advanced through a blood vessel such as the aorta A to a position adjacent to the ostium O of a (e.g., left and/or right) coronary artery CA as illustrated in FIG. 1. When so positioned, a treatment catheter (e.g., balloon catheter, stent delivery system, etc.) may be advanced through guide catheter 10 and into the coronary artery CA to a target location where the treatment catheter may be used to perform the appropriate cardiac intervention.

In order for the treatment catheter to efficiently reach the intended target location, maintaining the position of guide catheter 10 at the ostium O of the coronary artery CA may be desirable. For example, given that the heart may be beating during the intervention (and/or other factors), the guide catheter 10 may lose its positioning or otherwise be shifted so that it no longer is positioned to efficiently guide the treatment catheter to the coronary arteries. This may include a distal end 12 of guide catheter 10 being shifted away from the ostium O of the coronary artery CA. Because of the shift away from the ostium O, access to the coronary arteries CA may require repositioning of guide catheter 10 in order to bring the distal end 12 back into engagement with the ostium O of the coronary artery CA.

Figure 2:
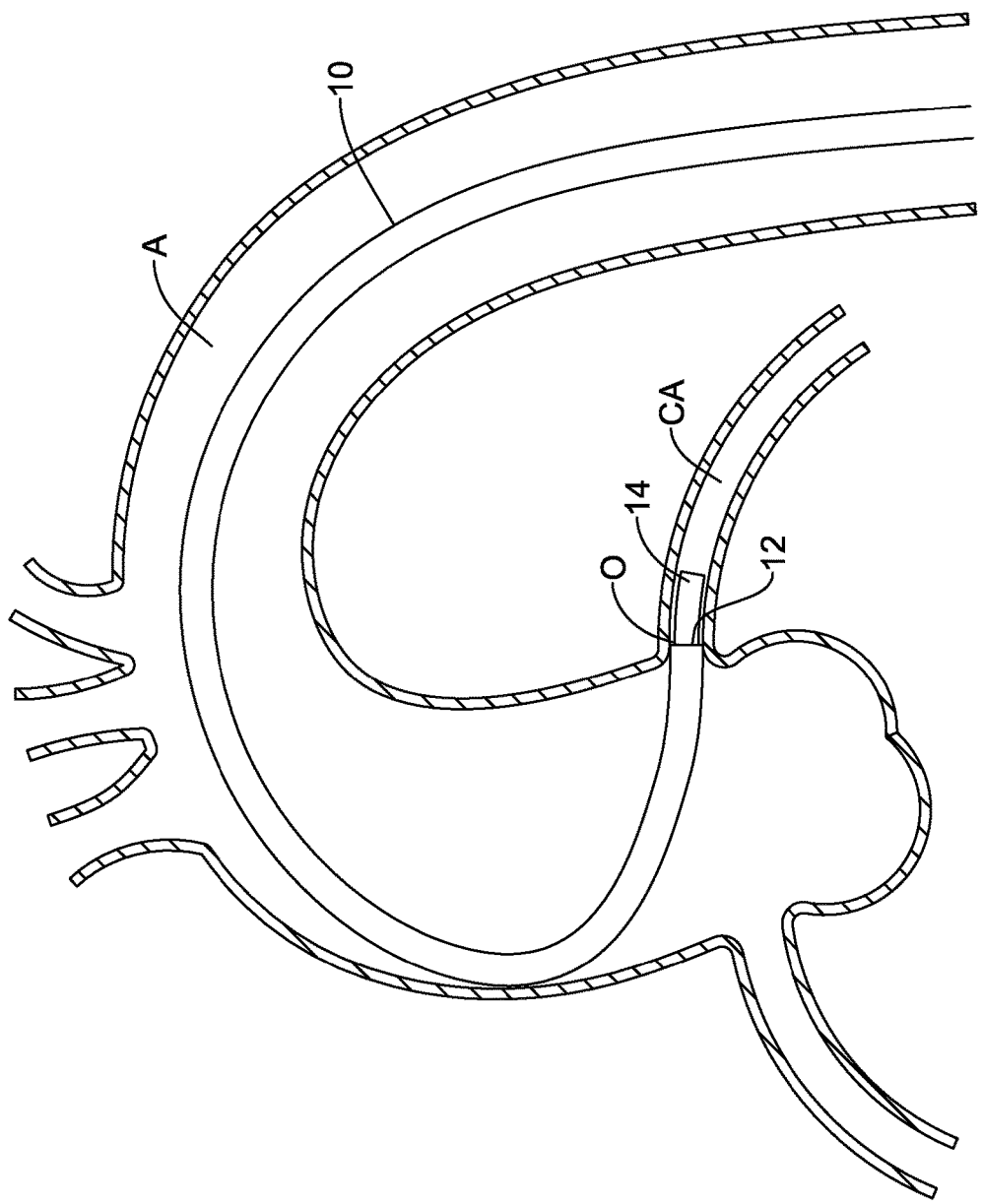
FIG. 2 is a plan view illustrating an example guide extension catheter used in conjunction with a guide catheter.

Disclosed herein are medical devices and methods for making and using medical devices that may improve access to the coronary arteries CA. For example, FIG. 2 illustrates a guide extension catheter 14 extending through guide catheter 10 and beyond distal end 12 of guide catheter 10 into the coronary artery CA. Because, for example, guide extension catheter 14 may extend beyond distal end 12 of guide catheter 10, guide extension catheter 14 may extend beyond the ostium O of the coronary artery CA and into a portion of the coronary artery CA. By extending beyond the ostium O, the extension catheter 14 may stabilize the positioning of guide catheter 10 and allow for improved access to the coronary artery CA for a number of cardiac interventions.

Figure 3:
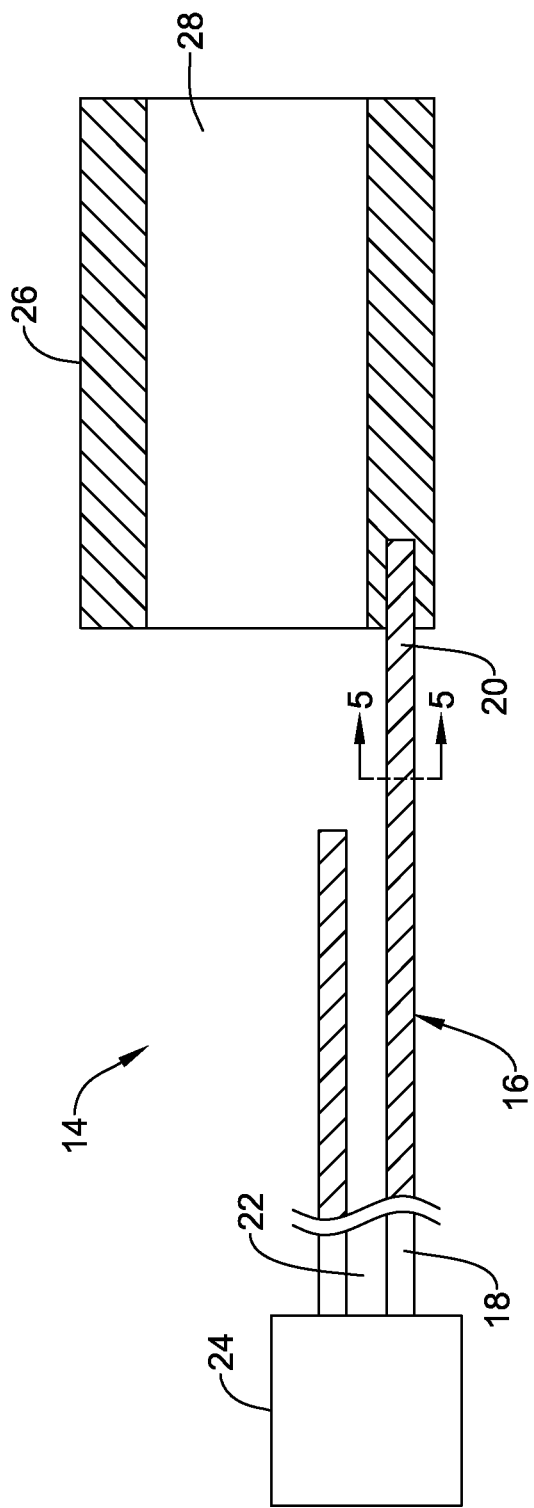
FIG. 3 is a cross-sectional side view of an example guide extension catheter.

FIG. 3 is a cross-sectional side view of guide extension catheter 14. Here it can be seen that guide extension catheter 14 may include a push member 16. Push member 16 may include a proximal portion 18 and a distal or ribbon portion 20. Proximal portion 18 may have a lumen 22 defined therein. In some embodiments, lumen 22 extends along the entire length of proximal portion 18. In other embodiments, lumen 22 extends along only a portion of the length of proximal portion 18. In addition, proximal portion 18 may include both proximal and distal openings (e.g., positioned at the proximal and distal end of proximal portion 18) such that lumen 22 is "open" on both ends. Alternatively, one or both of the ends of proximal portion 18 may be closed or otherwise sealed. For example, the distal end of proximal portion 18 may be closed. In some of these and in other embodiments, proximal portion 18 may have an opening or port (not shown) formed in the wall of proximal portion 18 and spaced from the proximal and/or distal end of proximal portion 18. The port may or may not be in fluid communication with lumen 22. A hub 24 may be attached to proximal portion 18.

A distal sheath 26 may be attached to push member 16. Sheath 26 may have a lumen 28 formed therein. In general, lumen 28 (and/or the inner diameter of distal sheath 26) may be larger than lumen 22 (and/or the inner diameter of proximal portion 18) and may be larger than the outer diameter of push member 16. Accordingly, lumen 28 may be sufficiently large so as to allow a therapeutic catheter (e.g., balloon catheter, stent delivery system, etc.) to pass therethrough. For example, when guide extension catheter 14 is positioned within guide catheter 10, the therapeutic catheter may extend within guide catheter 10 alongside push member 16 and through lumen 28 of distal sheath 26.

Distal sheath 26 may be attached to ribbon portion 20 of push member 16. The arrangement and/or configuration of the attachment between ribbon portion 20 and distal sheath 26 may vary. For example, distal sheath 26 may have an opening or lumen formed in tube wall thereof and ribbon portion 20 may be disposed within the opening. This may include necking or pinching down ribbon portion 20 and inserting the necked down portion into the opening. In some embodiments, inserting ribbon portion 20 into the opening may secure push member 16 to distal sheath 26 via a mechanical bond. In some of these and in other embodiments, additional and/or alternative bonding may be utilized including those bonding mechanisms commonly used for medical devices (e.g., adhesive bonding, welding, thermal bonding, brazing, etc.). Other attachment mechanisms are also contemplated for attaching push member 16 to distal sheath 26 including direct bonding (e.g., adhesive bonding, thermal bonding, welding, brazing, etc.), bonding that is facilitated by a third component (e.g., a metal or polymer collar bonded between the ribbon portion 20 and distal sheath 26), or the like.

Guide extension catheter 14 may also include a number of coatings that may, for example, reduce friction. For example, push member 16 may have an inner and/or outer coating that includes a hydrophilic polymer that may reduce friction during tracking. An example coating may include BAYER CL-100, BIOSLIDE, NG-HPC, SLIP COAT, MDX, or the like. These are just examples. Other materials are contemplated including those disclosed herein.

Figure 4:
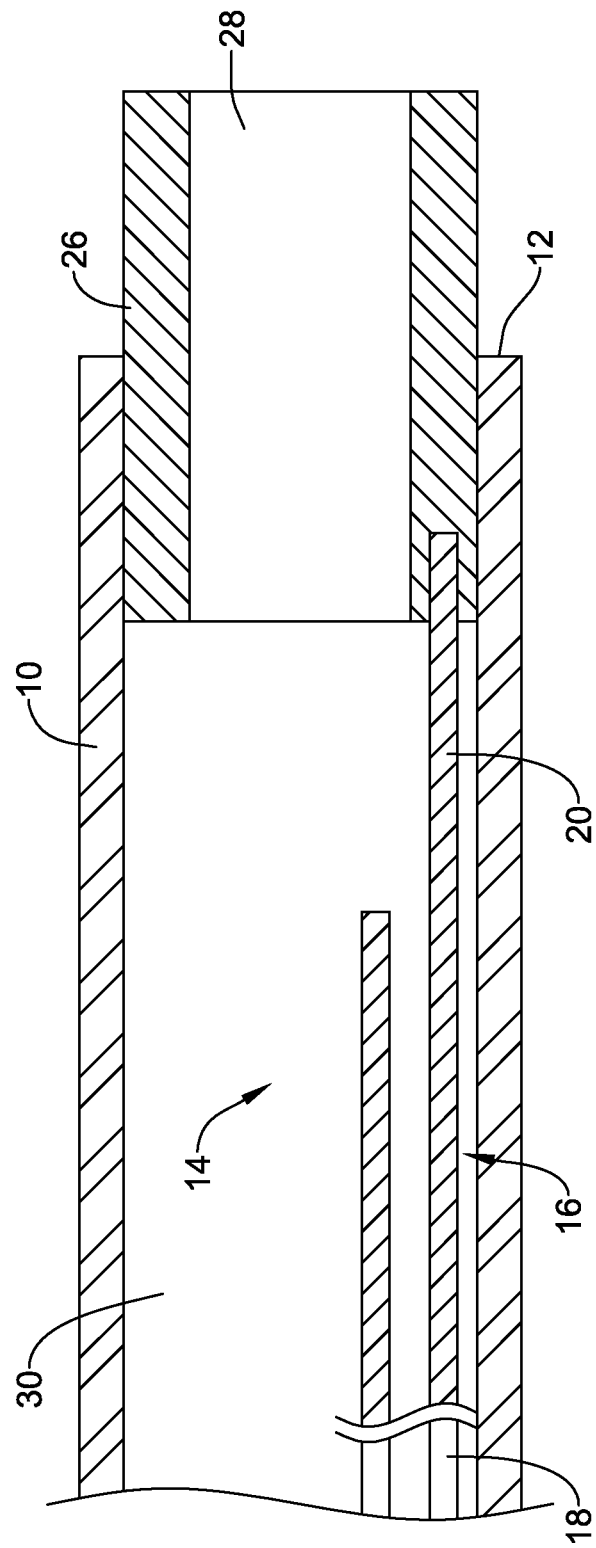
FIG. 4 is a cross-sectional view taken through line 4-4 in FIG. 3.

FIG. 4 illustrates guide extension catheter 14 disposed within guide catheter 10 (e.g., disposed within a lumen 30 defined within guide catheter 10). As shown, distal sheath 26 may be arranged to extend distally out from distal end 12 of guide catheter 10. When so arranged, distal sheath 26 may engage the ostium O and/or extend within a portion of the coronary artery CA to help maintain the position of guide catheter 10 and improve access to the coronary artery CA. Push member 16 may be designed to be sufficiently small (while still being sufficiently sized and configured for pushability) so as to take up relatively little space within the interior or lumen 30 of guide catheter 10. Accordingly, the use of guide extension catheter 14 allows for a therapeutic catheter or medical device to be advanced through guide catheter 10 in order to reach the desired target location for the intervention. In some embodiments, push member 16 may contact the inner wall surface of guide catheter 10, which may provide even more space.

Figure 5:
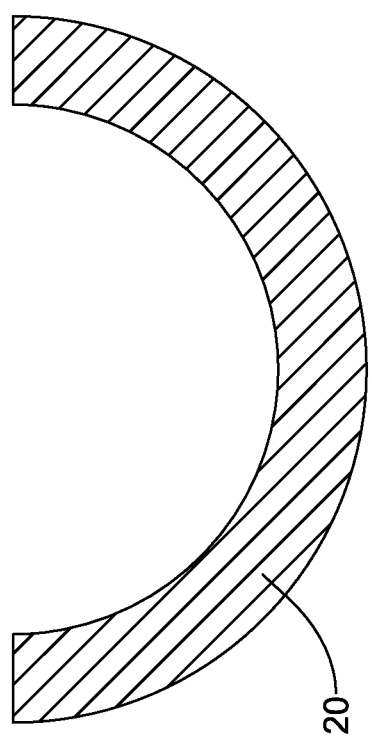
FIG. 5 is a cross-sectional side view of the example guide extension catheter and an example guide catheter.

FIG. 5 is a cross-sectional view of ribbon portion 20. Here it can be seen that ribbon portion 20 may have an arcuate or curved shape. The shape of ribbon portion 20 may be desirable for a number of reasons. The arcuate shape may increase the push force and the torque control of ribbon portion 20 as compared to a flat rectangular ribbon. For example, a flat rectangular ribbon (e.g., a 0.010 inch thick ribbon) may provide about 25 g of push force whereas ribbon portion 20 may provide a push force that is about 25% to 175 or about 40% to 150%, or about 50% to 150% more than the push force of a flat rectangular ribbon. In some embodiments, ribbon portion 20 may provide about 100 to 200 g of push force, or about 125 to 200 g of push force, or about 150 to 200 g of push force, or about 170 g of push force. These are just examples. While ribbon portion 20 is illustrated as having an arcuate shape, this is not intended to be limiting as the shape and/or configuration of ribbon portion 20 may vary and additional shapes are contemplated.

Ribbon portion 20 may also be thinner than conventional rectangular ribbons (e.g., conventional rectangular ribbons having a thickness of about 0.010 inches or more). For example, ribbon portion 20 may have a thickness in the range of about 0.005 to 0.010 inches, or about 0.006 to 0.008 inches, or about 0.007 inches. The smaller size in combination with the arcuate shape may allow ribbon portion 20 to be relatively highly flexible while still maintaining good pushability. The smaller size may also free up more space with guide catheter 10 for other devices. In addition, the rounded profile of ribbon portion 20 may generally trace the inner surface of guide catheter 10 (and/or a blood vessel), further increasing available space. Furthermore, the rounded shape may be smoother and/or sleeker than rectangular ribbons and may reduce trauma or damage to guide catheter 10 and/or the vasculature that could occur with other ribbons.

The arcuate shape of ribbon portion 20 may also provide coaxial guiding support for a device (e.g., a therapeutic catheter) being advanced through guide catheter 10 and along guide extension catheter 14. For example, the therapeutic device may be guided within the groove defined by the arcuate shape of ribbon portion 20 and ride in the groove like a "rail".

Manufacturing ribbon portion 20 may occur in a number of different manners. For example, ribbon portion 20 may fabricated by cutting (e.g., laser cutting) a portion of a tube. In doing so, a tube may be provided and a portion of the tube (e.g., a distal portion) may be cut away, thereby defining proximal portion 18 and ribbon portion 20. Other manufacturing processes may be utilized including processes where proximal portion 18 and ribbon portion 20 are separately provided and secured together using a suitable attachment technique.

Figure 6:
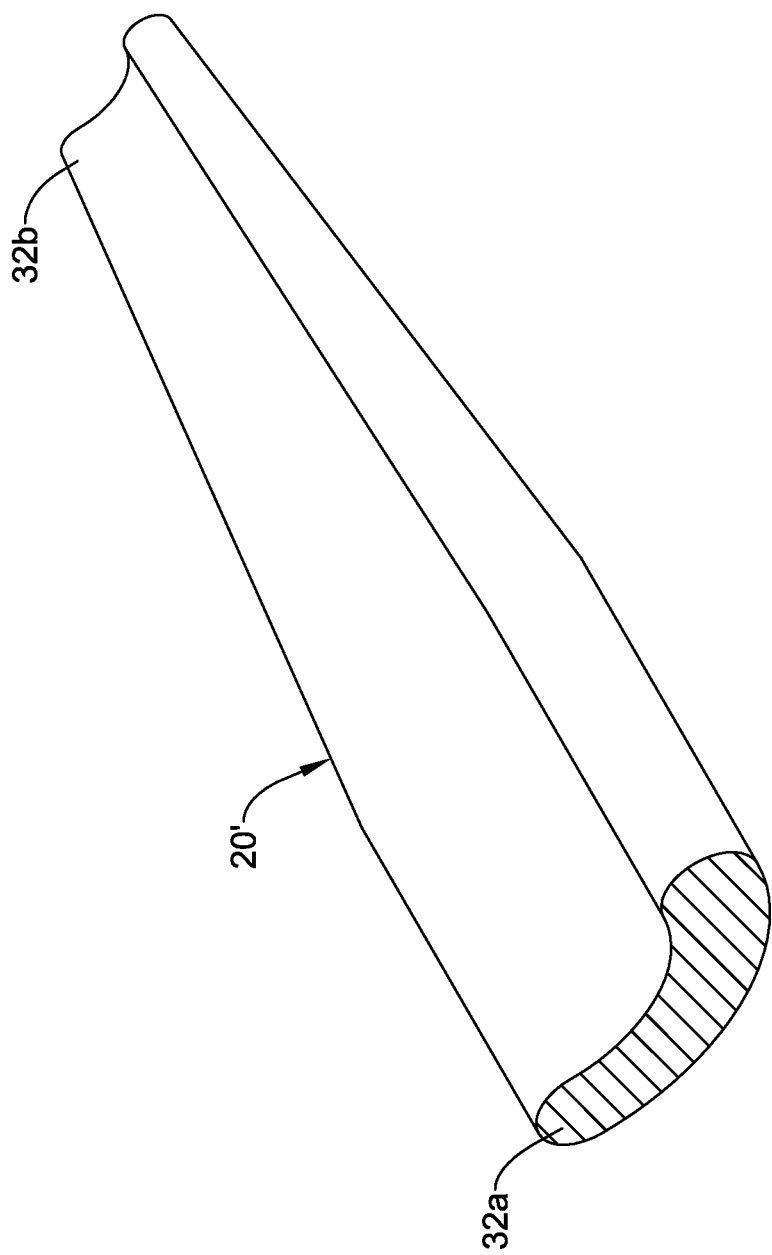
FIG. 6 is a partial cross-sectional view of a portion of an example guide extension catheter.

In some embodiments, ribbon portion 20 may have the same shape along its length. In other embodiments, the shape of ribbon portion 20 may vary along its length. For example, FIG. 6 illustrates ribbon portion 20' that tapers between a first end or portion 32a and a second end or portion 32b. The taper in ribbon portion 20' may be desirable for a number of reasons. For example, the taper may provide a gradual transition in flexibility along the length of ribbon portion 20. In addition, a tapered transition (similar to what is shown in FIG. 6) may be utilized at the transition between proximal portion 18 and ribbon portion 20. For example, the taper of ribbon portion 20' may begin a nearly tubular configuration near proximal portion 18 (e.g., which may be at first end 32a) and gradually taper to a less tubular and more arcuate configuration. This may improve the flexural profile of guide extension catheter 14 and reduce or eliminate sharp or abrupt transitions in flexibility, which could create kink points or abrupt bends.

Figure 7:
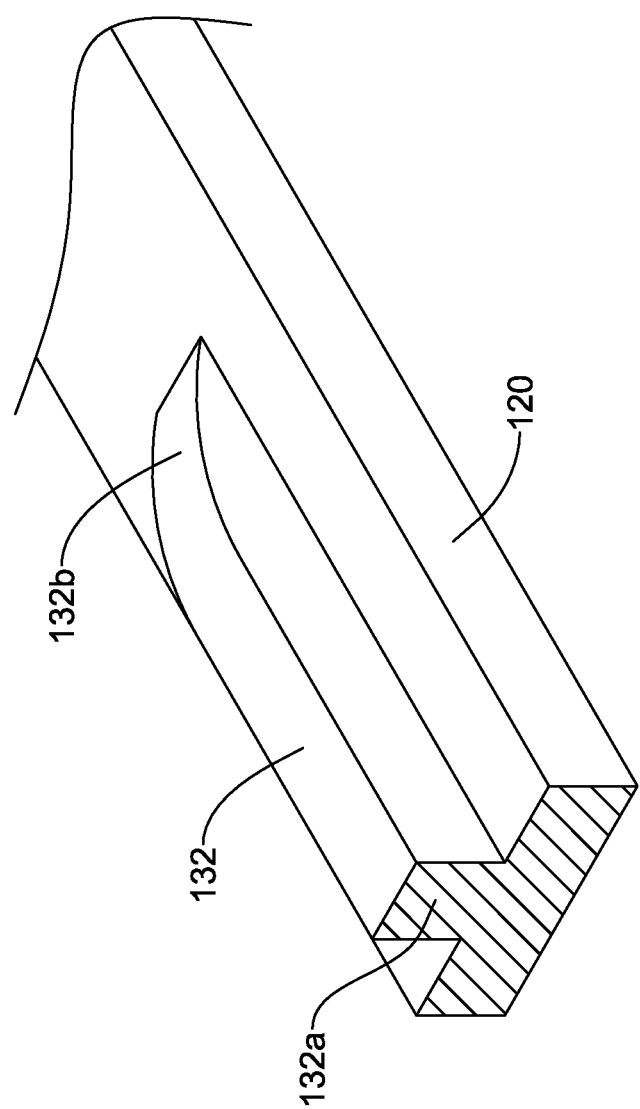
FIG. 7 is a partial cross-sectional view of a portion of another example guide extension catheter.

A portion of another example ribbon portion 120 is shown in FIG. 7. Here it can be seen that ribbon portion 120 may include a ridge 132. In at least some embodiments, ridge 132 may be T-shaped or include a section that is T-shaped. Ridge 132 may taper between first end or portion 132a and second end or portion 132b (where ridge 132 reduces in size or is eliminated altogether). Much like ribbon portion 20', the configuration of ribbon portion 120 may provide a gradual transition in flexibility along its length. The tapering or transition of ridge 132 may also be utilized at the transition between proximal portion 18 and ribbon portion 120 to further improve the flexural profile.

Figure 8:
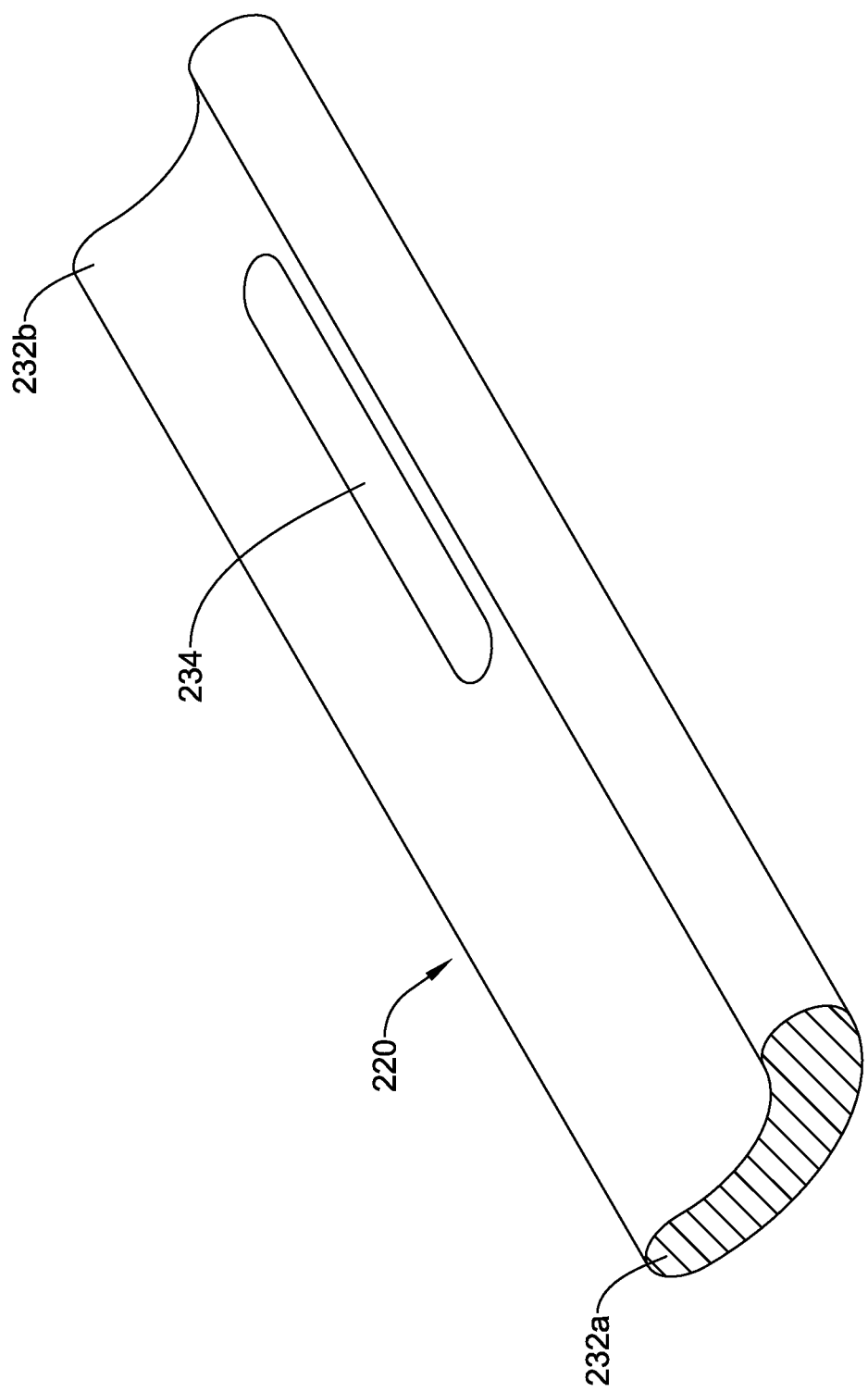
FIG. 8 is a partial cross-sectional view of a portion of another example guide extension catheter.

FIG. 8 illustrates another example ribbon portion 220. Ribbon portion 220 may include an opening or aperture 234 formed therein. Opening 234 may be positioned between first end or portion 232a and second end or portion 232b. Much like in ribbon portions 20'/120, opening 234 in ribbon portion 220 may provide a gradual transition in flexibility along its length. This may be further enhanced by altering the shape of opening 234. For example, opening 234 may be tapered. The tapering or transition of opening 234 may also be utilized at the transition between proximal portion 18 and ribbon portion 220 to further improve the flexural profile.

Figure 9:
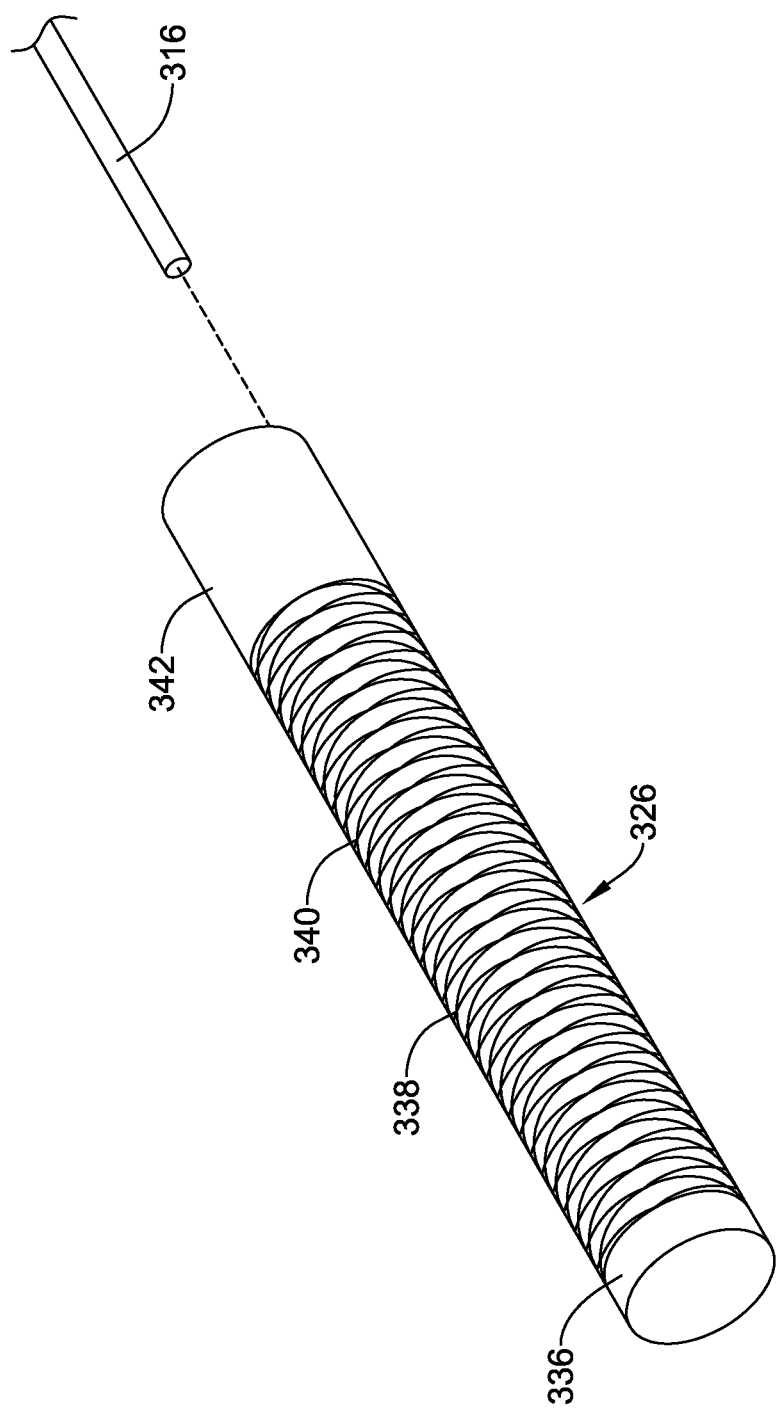
FIGS. 9-11 illustrate an example method for manufacturing a guide extension catheter.
Figure 10:
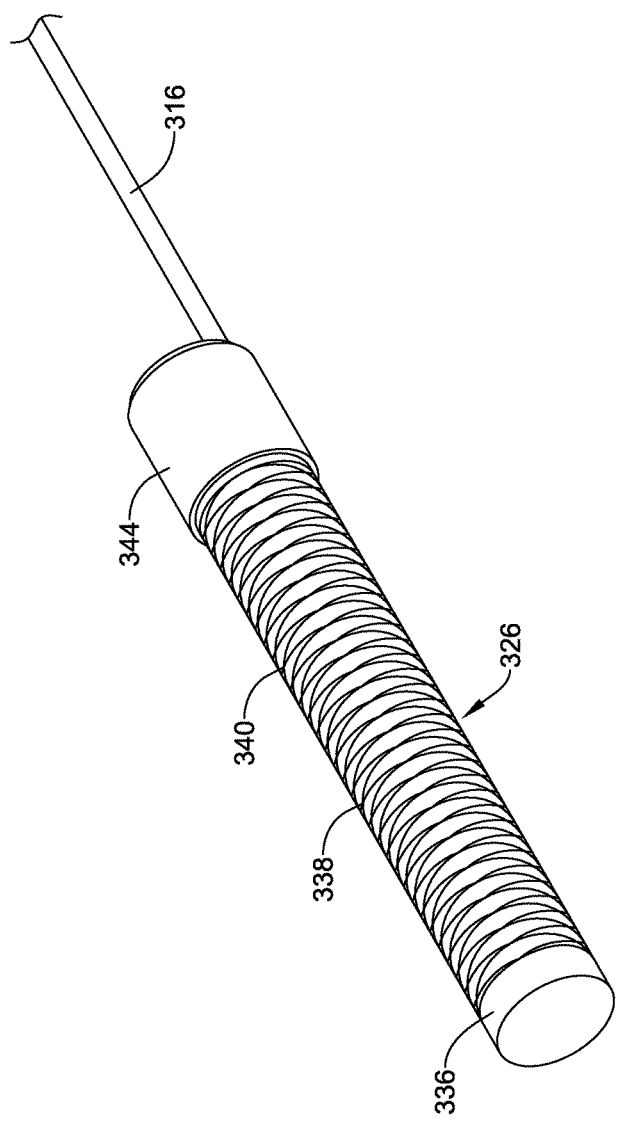
Figure 11:
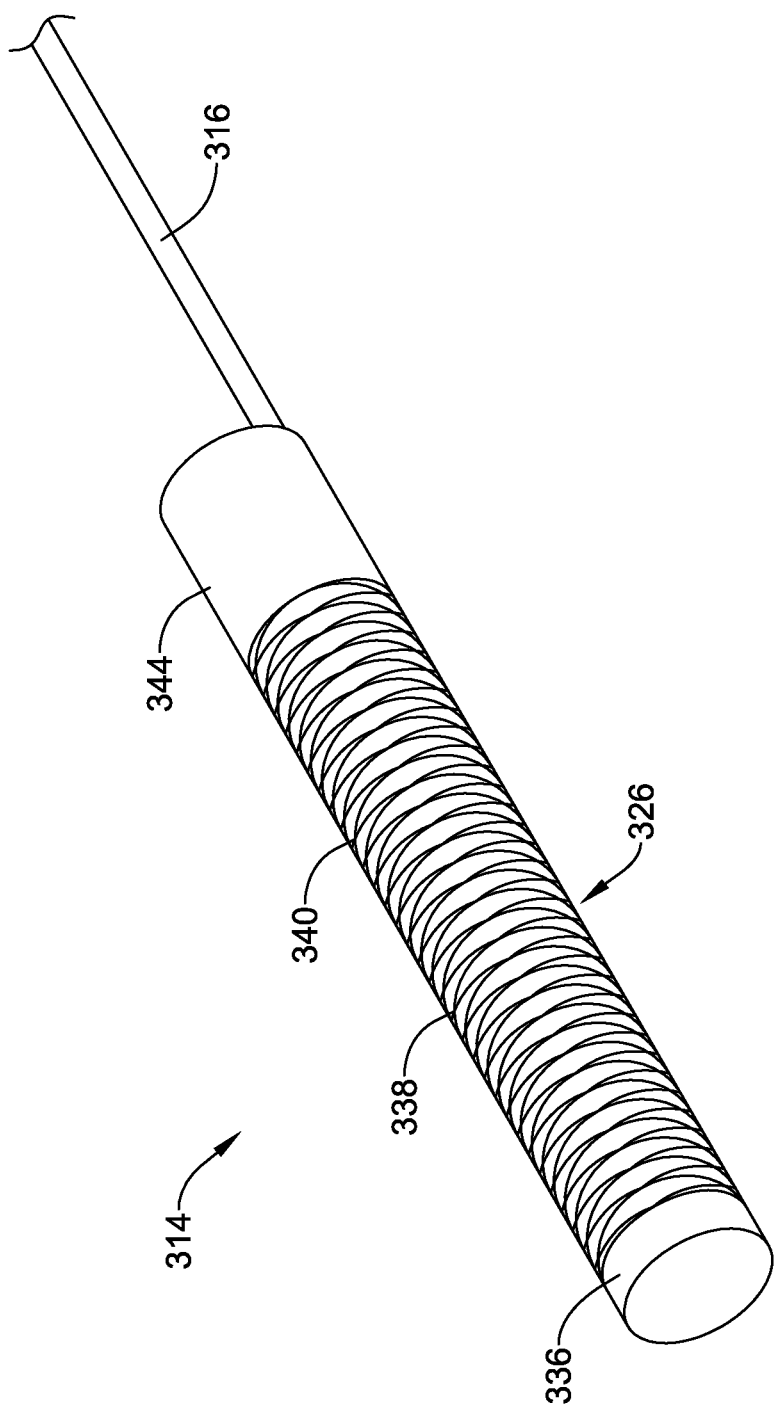

FIGS. 9-11 illustrate an example method for manufacturing an example guide extension catheter 314, which may be similar in form and function to other guide extension catheters disclosed herein. In this example, guide extension catheter 314 may include distal sheath 326 coupled to or otherwise attached to push member 316. Distal sheath 326 may include a distal region 336, a reinforced region 338 including a reinforcing member 340, and a proximal region 342. Reinforcing member 340 may include a braid, a coil, a mesh, or the like. In at least some embodiments, regions 336/342 may lack reinforcing member 340. Other forms of sheath 326 are contemplated.

To attach push member 316 to distal sheath 326, push member 316 may be disposed along an outer surface of distal sheath 326 and a polymeric sleeve 344 may be disposed about distal sheath 326 and push member 316 as shown in FIG. 10. Alternatively, push member 316 may be disposed along an inner surface of distal sheath 326 and sleeve 344 may be disposed about distal sheath 326 and push member 316. In either case, push member 316 and distal sheath 326 can be secured by a reflow method where sleeve 344 is reflowed, forming guide extension catheter 314 (e.g., as shown in FIG. 11). This effectively encapsulates or "sandwiches" push member 316 between the reflowed portion of distal sheath 326 and sleeve 344 that essentially form a unitary or singular structure.

The use of sleeve 344 in manufacturing guide extension catheter 314 may be desirable for a number of reasons. For example, the use of sleeve 344 may permit push member 316 and distal sheath 326 to be secured to one another without the use of an intermediate metallic and/or polymeric structure, which may add bulk and stiffness to the design as well as increased manufacturing costs including costs associated with fabricating the intermediate metallic structure (e.g., laser cutting, welding, gluing, or the like). Devices including the intermediate metallic structure may also be susceptible to failure when exposed to a wet environment. Thus, the use of sleeve 344 may allow the manufacturing process to use less material, less expensive materials, and fewer manufacturing steps. In addition, devices formed using the method disclosed herein may be more resistant to degradation in a wet environment. Furthermore, the use of sleeve 344 may be relatively easy to adapt to differently sized components, which may allow for the same manufacturing process to be used across differently sized product families.

The connection formed by sleeve 344 may also provide a desirable amount of tensile strength. For example, guide extension catheter 314 may be able to withstand tensile loads of about 2-10 pounds, or about 3 to 8 pounds, or about 4 to 7 pounds, or about 5 pounds or more. The connection may also be formed without forming a sharp or abrupt transition in flexibility. In other words, because sleeve 344 may be sufficiently flexible, the connection point between push member 316 and distal sheath 326 may be formed without defining a potential kink point. In addition, sleeve 344 can help form a gradual transition or gradient in flexibility across the connection point.

Figure 12:
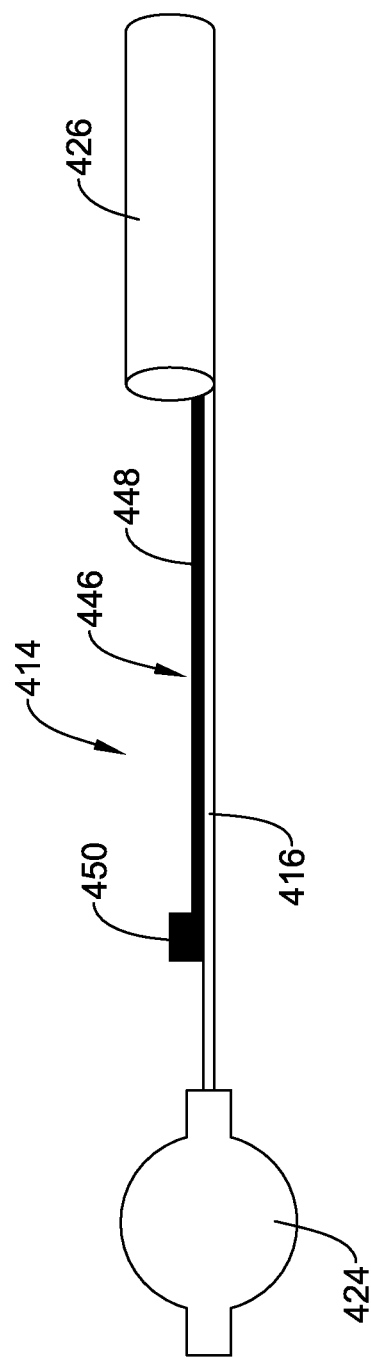
FIG. 12 is a side view of another example guide extension catheter.

FIG. 12 illustrates another example guide extension catheter 414 that may be similar in form and function to other guide extension catheters disclosed herein. Guide extension catheter 414 may include a ribbon member 416 that is attached to proximal hub 424 and distal sheath 426. Ribbon member 416 may vary in form. In some embodiments, ribbon member 416 may be tubular and include a lumen. The lumen may extend along substantially the full length of ribbon member 416 or along only a portion of the length of ribbon member 416. In other embodiments, ribbon member 416 may take the form of a ribbon or shaft. In these embodiments, the shape of ribbon member 416 may vary. For example, ribbon member 416 may have a cross-sectional shape that is a polygon (e.g., triangle, quadrilateral, square, rectangle, pentagon, hexagon, or the like). In some of these and in other embodiments, ribbon member 416 may have a cross-sectional shape that is circular, partially circular or rounded, or the like.

A removable push member 446 may be coupled to ribbon member 416. Removable push member 446 may include a body portion 448 and a proximal grip member 450. In general, push member 446 may be configured to provide additional "push" support during delivery of guide extension catheter 414. Accordingly, push member 446 can be coupled to ribbon member 416 during delivery. As suggested by the name, removable push member 446 may be removably coupled to ribbon member 416. Thus, when guide extension catheter 414 is delivered to the desired location, removable push member 446 may be separated from ribbon member 416 and "removed".

Figure 13:
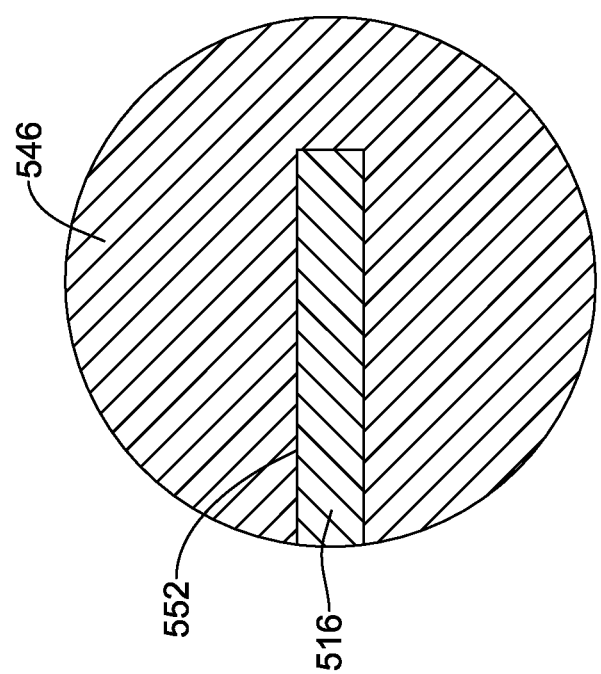
FIG. 13 is a cross-sectional view of a portion of an example guide extension catheter.

The precise arrangement of removable push member 446 and ribbon member 416 may vary. In general, the shape of push member 446 and/or ribbon member 416 may be configured so that push member 446 and ribbon member 416 can remain suitably coupled during delivery and then easily separated from one another when delivered. For example, FIG. 13 illustrates ribbon member 516 in the form of a relatively flat, rectangular ribbon. Removable push member 546 includes a channel 552 configured to house ribbon member 516. According to this embodiment, ribbon member 516 and push member 546 can be coupled to one another, for example, by disposing ribbon member 516 within channel 552 of push member 546. When advanced (e.g., through a guide catheter) to the desired location, push member 546 can be removed. This may include proximally retracting push member 546 relative to ribbon member 516.

Figure 14:
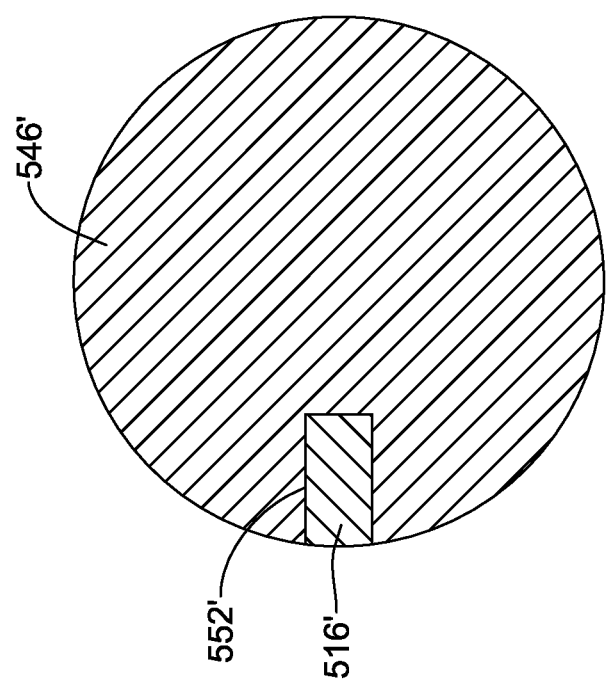
FIG. 14 is a cross-sectional view of a portion of another example guide extension catheter.

Removable push member 546 may be configured to be relatively easily removed from ribbon member 516. This may be desirable for a number of reasons including, for example, ease of use. In addition, because push member 546 and ribbon member 516 can be easily uncoupled, the relative sizes of removable push member 546 and/or ribbon member 516 may be altered to meet the goals of a given intervention. For example, FIG. 14 illustrates a relatively smaller ribbon member 516' coupled to removable push member 546'. In this example, channel 552' is sized to accommodate the relatively smaller ribbon member 516'. Here it can be seen that the use of a removable push member (e.g., removable push member 546' or other removable push members disclosed herein) may allow small structures that might not otherwise provide a sufficient push force to deliver a guide extension catheter (but may take up relatively little space within guide catheter 10) to be structurally reinforced with removable push member 546'. When suitably delivered, removable push member 516' can be removed, leaving behind the relatively small ribbon member 516', which may free up additional space within guide catheter 10.

Figure 15:
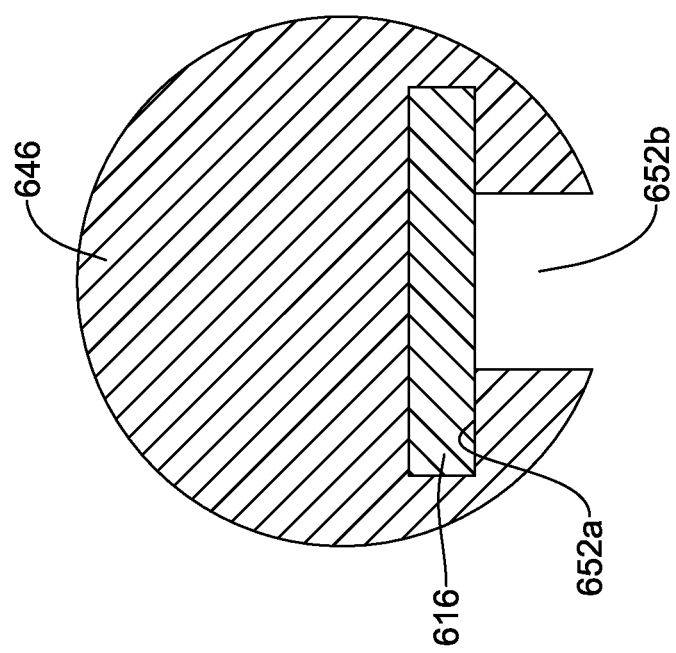
FIG. 15 is a cross-sectional view of a portion of another example guide extension catheter.

FIG. 15 illustrates an alternative arrangement that may be used with any of the guide extension catheters disclosed herein. According to this embodiment, removable push member 646 may include opening 652a that is sized to accommodate ribbon member 616. Removable push member 646 may also include another opening 652b. Opening 652b may provide additional flexibility to push member 646, which may facilitate removal of push member 646 from ribbon member 616. The size and shape of opening 652b may vary. For example, opening 652b may have a width that approximates the width of ribbon member 616 or opening 652b may have a width that is smaller than the width of ribbon member 616.

Figure 16:
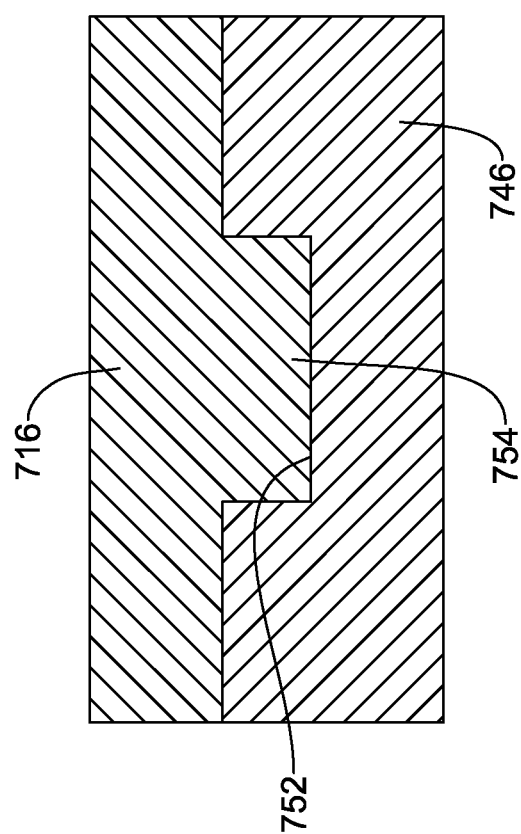
FIG. 16 is a cross-sectional view of a portion of another example guide extension catheter.

FIG. 16 illustrates an alternative arrangement that may be used with any of the guide extension catheters disclosed herein. According to this embodiment, removable push member 746 may include a channel 752. Ribbon member 716 may include a ridge or rail 754. In this example, channel 752 may be configured to accommodate rail 754. Thus, in use, rail 754 and channel 752 may be brought together in a mating relationship during delivery and separated from one another, if desired, when delivery is complete. While the shape and configuration of rail 754 and channel 752 are depicted in FIG. 16 as being rectangular, this is not intended to limiting. A wide variety of shapes are contemplated including shapes that include more than one rail 754 and/or channel 752, differently shaped or oriented rails 754 and/or channels 752, or the like.

Figure 17:
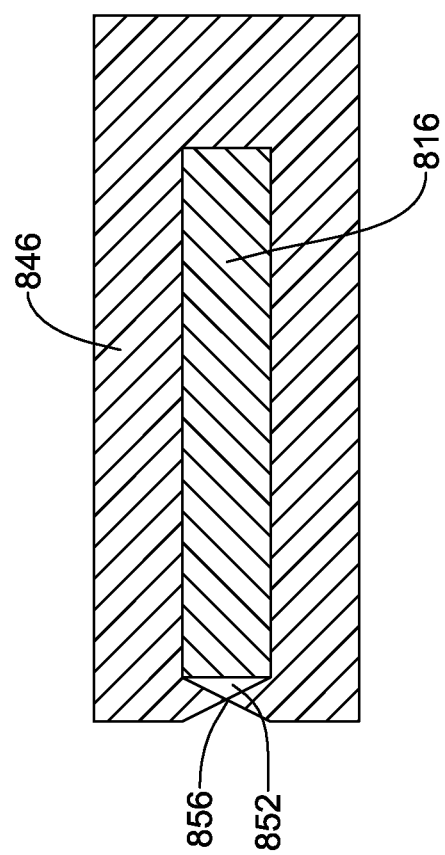
FIG. 17 is a cross-sectional view of a portion of another example guide extension catheter.

FIG. 17 illustrates an alternative arrangement that may be used with any of the guide extension catheters disclosed herein. For example, removable push member 846 may include a channel 852 having an opening 856. In this example, channel 852 may be configured to accommodate ribbon member 816. Opening 856 may be configured to flex or widen so as to facilitate coupling of ribbon member 816 and push member 846. Just like other push members and ribbon members disclosed herein, the shape, configuration, form, etc. of push member 846 and ribbon member 816 may vary.

Figure 18:
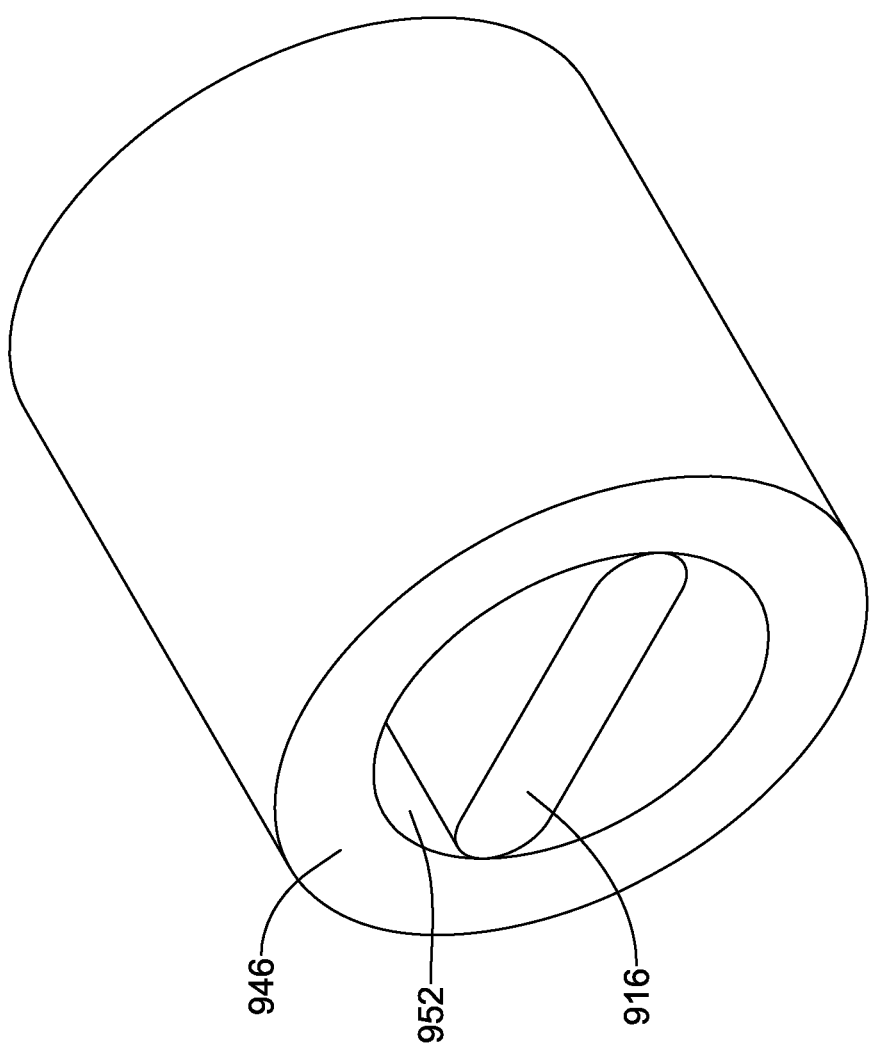
FIG. 18 is a perspective view of a portion of another example guide extension catheter.

FIG. 18 illustrates an alternative arrangement that may be used with any of the guide extension catheters disclosed herein. According to this embodiment, removable push member 946 may take the form of a tube that has a channel or lumen 952 formed therein. Lumen 952 may be configured to accommodate ribbon member 916. Thus, push member 946 may be disposed about ribbon member 916, for example during delivery, and removed from ribbon member 916 as desired.

Figure 19:
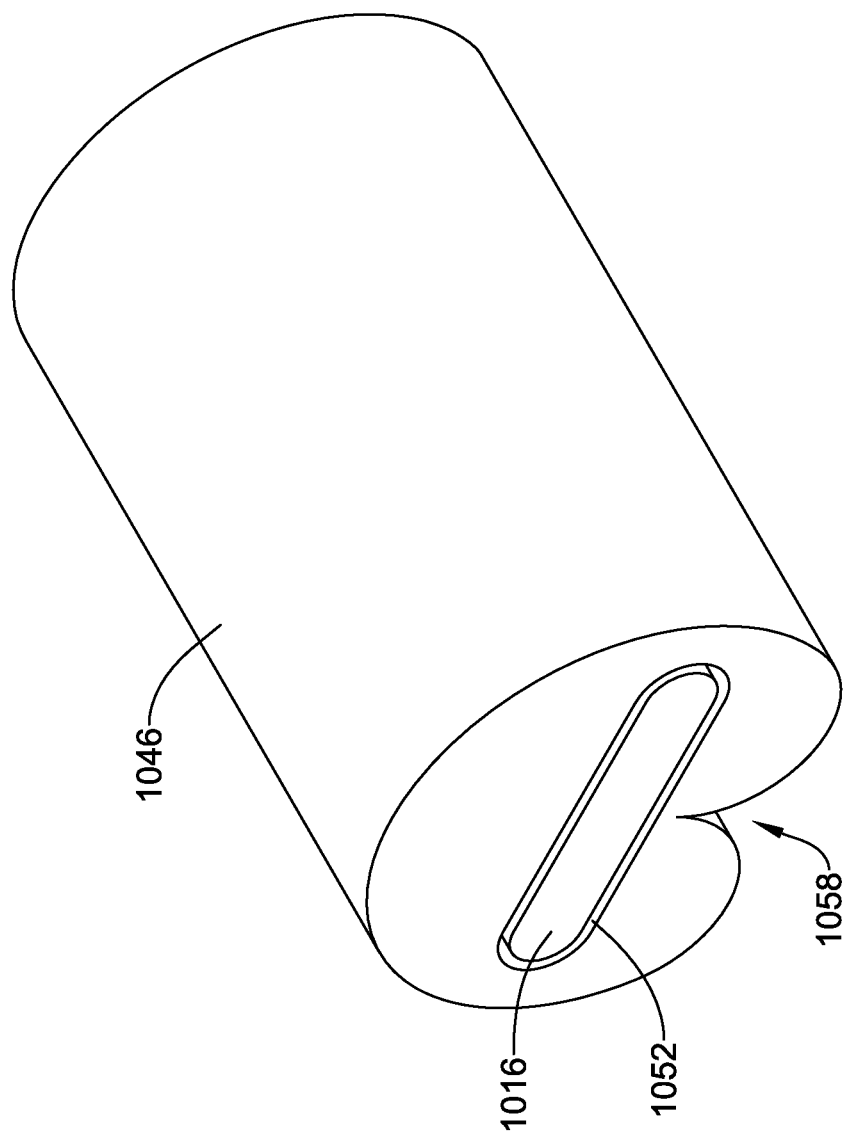
FIG. 19 is a perspective view of a portion of another example guide extension catheter.

FIG. 19 illustrates an alternative arrangement that may be used with any of the guide extension catheters disclosed herein. According to this embodiment, removable push member 1046 may take the form of a tube that has a channel or lumen 1052 formed therein. Lumen 1052 may be configured to accommodate ribbon member 1016. A zip seam 1058 may be formed in removable push member 1046 that is configured to open up in order to allow a user to move ribbon member 1016 into and out from channel 1052. For example, zip seam 1058 may be configured to widen or "open" such that ribbon member 1016 may be more easily shifted (e.g., removed from) relative to push member 1046. In some embodiments, adjacent edges of zip seam 1058 may contact one another. In other embodiments, a gap may be formed between the edges of zip seam 1058.

Figure 20:
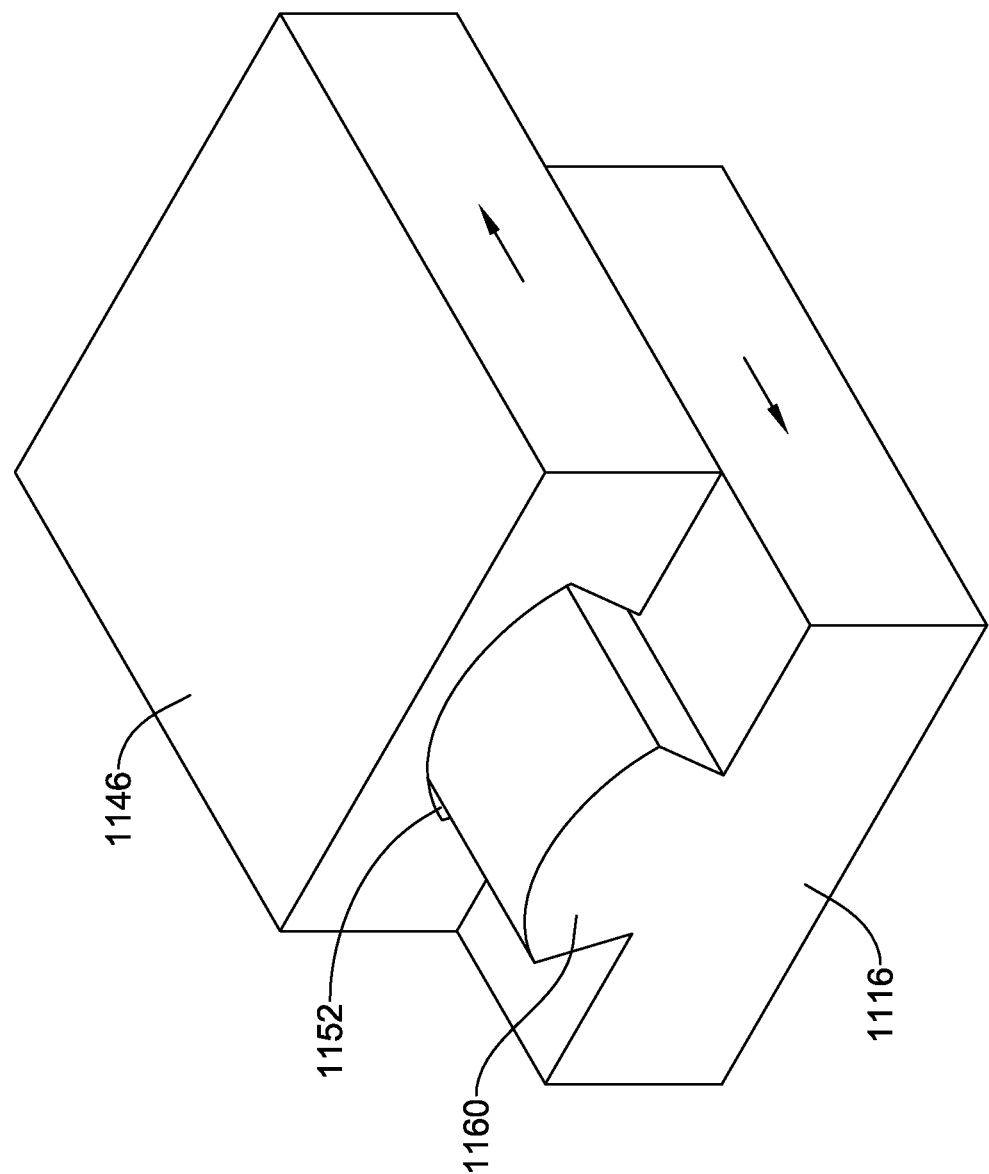
FIG. 20 is a perspective view of a portion of another example guide extension catheter.

FIG. 20 illustrates an alternative arrangement that may be used with any of the guide extension catheters disclosed herein. For example, removable push member 1146 may include a channel 1152. In this example, channel 1152 may be configured to accommodate a ridge or rail 1160 formed on ribbon member 1116. Much like other embodiments disclosed herein, rail 1160 and channel 1152 may vary and include a variety of shapes and/or configurations. For example, in at least some embodiments, rail 1160 may extend along substantially the full length of ribbon member 1116. In other embodiments, a portion of rail 1160 may be removed from ribbon member 1116. For example, a relatively short length (e.g., in the range of about 1 to 5 inches or so) of rail 1160 along a proximal portion of ribbon member 1116 may be removed. This may make it easier to shift the position of push member 1146 relative to ribbon member 1116.

Figure 21:
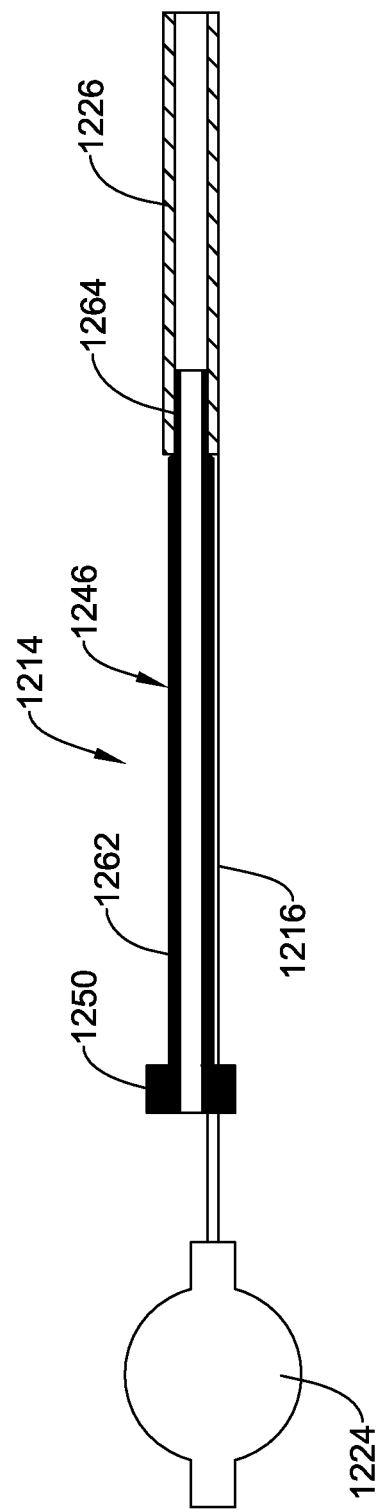
FIG. 21 is a partial cross-sectional side view of another example guide extension catheter.
Figure 22:
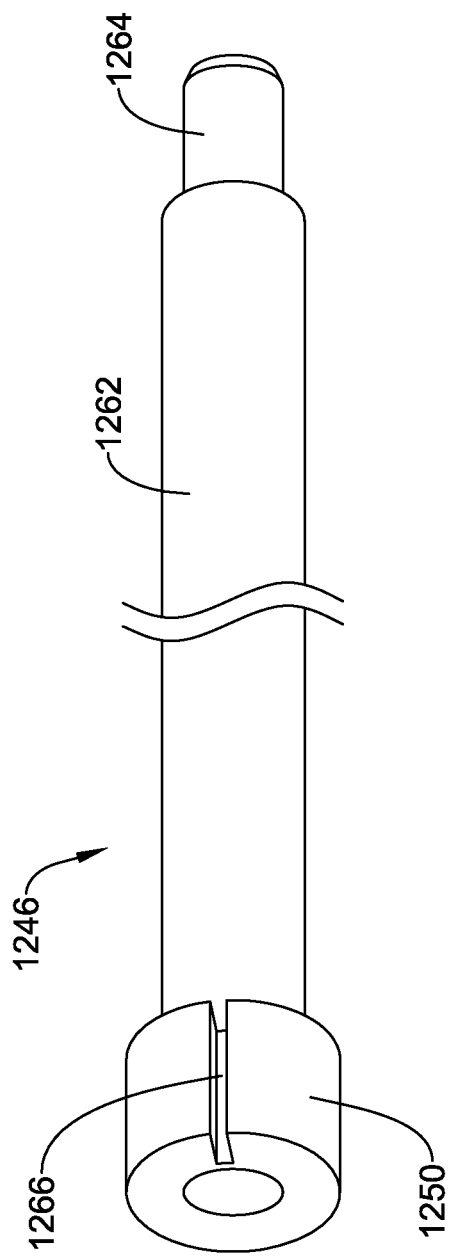
FIG. 22 is a perspective view of a portion of example guide extension catheter illustrated in FIG. 21.

FIG. 21 illustrates another example guide extension catheter 1214 that may be similar in form and function to other guide extension members disclosed herein. Guide extension member 1214 may include ribbon member 1216 having hub 1224 and distal sheath 1226 attached thereto. Removable push member 1246 may be removably coupled to ribbon member 1216. Removable push member 1246 may include a tubular proximal portion 1262 and a tubular distal portion 1264. A hub 1250 may be coupled to tubular proximal portion 1262. Hub 1250 may have a slot 1266 formed therein that is configured to accommodate ribbon member 1216 as shown in FIG. 22.

Removable push member 1246 may be configured to provide structural support to ribbon member 1216. In addition, because push member 1246 may include tubular distal portion 1264 that may extend into distal sheath 1226, push member 1246 may also provide structural support to distal sheath 1226 during delivery of guide extension catheter 1214. When guide extension catheter 1214 is suitably delivered to the desired position, push member 1246 can be removed.

The materials that can be used for the various components of the guide extension catheters disclosed herein may vary. For simplicity purposes, the following discussion makes reference to push member 16 and distal sheath 26. However, this is not intended to limit the devices and methods described herein, as the discussion may be applied to other similar tubular members and/or components of tubular members or devices disclosed herein.

Push member 16 and distal sheath 26 and/or other components of guide extension catheter 14 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of push member 16 and/or distal sheath 26 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guide extension catheter 14 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guide extension catheter 14 to achieve the same result.

In some embodiments, a degree of Magnetic Resonance Imaging (MRI) compatibility is imparted into guide extension catheter 14. For example, push member 16 and distal sheath 26, or portions thereof, may be made of a material that does not substantially distort the image and create substantial artifacts (i.e., gaps in the image). Certain ferromagnetic materials, for example, may not be suitable because they may create artifacts in an MRI image. Push member 16 and distal sheath 26, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of push member 16 and distal sheath 26 that may define a generally smooth outer surface for guide extension catheter 14. In other embodiments, however, such a sheath or covering may be absent from a portion of all of guide extension catheter 14, such that push member 16 and distal sheath 26 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guide extension catheter 14 (including, for example, the exterior surface of push member 16 and distal sheath 26) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of push member 16 and distal sheath 26, or other portions of guide extension catheter 14. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A guide extension catheter, comprising:
   a push member having a distal end portion with an arcuate cross-section and a decreasing radius of curvature from a proximal end to a distal end of the push member, the push member at the arcuate cross-section has an inner surface and an outer surface such that the inner surface is parallel to the outer surface;
   a distal tubular member attached to a distal end portion of the push member and extending distal of the push member, the distal tubular member comprising:
      a reinforced region having a reinforcing member; and
      a proximal region lacking the reinforcing member; and
   a sleeve disposed over the proximal region of the distal tubular member to attach the distal tubular member to the push member, wherein the distal end portion of the push member extends between the proximal region of the distal tubular member and the sleeve.

2. The guide extension catheter of claim 1, wherein the sleeve attaches the push member to the distal tubular member through a reflow connection.

3. The guide extension catheter of claim 1, wherein there is a gradual transition in flexibility between the push member and the distal tubular member.

4. The guide extension catheter of claim 1, wherein the proximal region of the distal tubular member is attached to the push member.

5. The guide extension catheter of claim 1, wherein the distal end portion of the push member includes an arcuate cross-section.

6. The guide extension catheter of claim 5, wherein the push member comprises a polymer material.

7. The guide extension catheter of claim 1, wherein the push member is attached to the distal tubular member along an outer surface of the distal tubular member.

8. The guide extension catheter of claim 1, wherein the reinforced region of the distal tubular member includes a coil.

9. The guide extension catheter of claim 1, wherein the reinforced region of the distal tubular member includes a braid.

10. A guide extension catheter, comprising:
    a push member having a distal end portion with an arcuate cross-section and a decreasing radius of curvature from a proximal end to a distal end of the push member, the push member at the arcuate cross-section has an inner surface and an outer surface such that the inner surface is parallel to the outer surface; and
    a distal tubular member attached to the distal end portion, wherein there is a gradual transition in flexibility between the push member and the distal tubular member.

11. The guide extension catheter of claim 10, wherein the distal tubular member includes a reinforcing region having a reinforcing member and a proximal region proximal the reinforcing region and lacking the reinforcing member.

12. The guide extension catheter of claim 11, wherein the distal end portion of the push member is attached to the proximal region of the distal tubular member.

13. The guide extension catheter of claim 11, wherein the reinforcing member includes a coil.

14. The guide extension catheter of claim 10, wherein the push member comprises a polymer material.

15. The guide extension catheter of claim 14, wherein the push member comprises a metal material.

16. A method for manufacturing a guide extension catheter, the method comprising:
    providing a proximal member having a distal end portion with an arcuate cross-section and a decreasing radius of curvature from a proximal end to a distal end of the proximal member, the proximal member at the arcuate cross-section has an inner surface and an outer surface such that the inner surface is parallel to the outer surface;
    providing a distal tubular member;
    disposing a polymeric tube over a distal end portion of the proximal member and a proximal region of the distal tubular member, wherein the distal end portion of the proximal member extends between the proximal region of the distal tubular member and the polymeric tube;
    reflowing the polymeric tube to form a joint that attaches the proximal member and the distal tubular member.

17. The method of claim 16, wherein the joint forms a gradual transition in flexibility from the proximal member to the distal tubular member.

18. The method of claim 16, wherein the distal tubular member includes a reinforced region with a reinforcing member and the proximal region is free of the reinforcing member, and wherein the joint attaches the proximal region free of the reinforcing member to the proximal member.

* * * * *